United States Patent
Ackerman et al.

(10) Patent No.: US 10,456,548 B2
(45) Date of Patent: Oct. 29, 2019

(54) INFLATION CONTROL VALVES FOR RESUSCITATOR DEVICES AND RESUSCITATOR DEVICES

(71) Applicants: Jeremy D. Ackerman, Atlanta, GA (US); Arthur L. Kellermann, Washington, DC (US); Sam Raji, Alpharetta, GA (US); Arsalan Sabooree, Suwanee, GA (US); Lintu Ramachandran, Atlanta, GA (US)

(72) Inventors: Jeremy D. Ackerman, Atlanta, GA (US); Arthur L. Kellermann, Washington, DC (US); Sam Raji, Alpharetta, GA (US); Arsalan Sabooree, Suwanee, GA (US); Lintu Ramachandran, Atlanta, GA (US)

(73) Assignee: Emory University, Atlanta, GA (US)

( * ) Notice: Subject to any disclaimer, the term of this patent is extended or adjusted under 35 U.S.C. 154(b) by 740 days.

(21) Appl. No.: 14/364,739

(22) PCT Filed: Dec. 14, 2012

(86) PCT No.: PCT/US2012/069791
§ 371 (c)(1),
(2) Date: Jun. 12, 2014

(87) PCT Pub. No.: WO2013/090746
PCT Pub. Date: Jun. 20, 2013

(65) Prior Publication Data
US 2014/0318545 A1    Oct. 30, 2014

Related U.S. Application Data

(60) Provisional application No. 61/576,160, filed on Dec. 15, 2011.

(51) Int. Cl.
*A61M 16/20* (2006.01)
*A61M 16/00* (2006.01)
*A61M 16/06* (2006.01)

(52) U.S. Cl.
CPC ...... *A61M 16/201* (2014.02); *A61M 16/0078* (2013.01); *A61M 16/0084* (2014.02); *A61M 16/208* (2013.01); *A61M 16/06* (2013.01)

(58) Field of Classification Search
CPC .............. A61M 16/00; A61M 16/0003; A61M 16/0048; A61M 16/0078; A61M 16/0084; A61M 16/06; A61M 16/20–16/209
See application file for complete search history.

(56) References Cited

U.S. PATENT DOCUMENTS

| 2,399,643 | A |   | 5/1946 | Kreiselman |
| 3,046,978 | A | * | 7/1962 | Lea ...................... A61M 16/00 128/205.13 |

(Continued)

OTHER PUBLICATIONS

International Search Report and Written Opinion for PCT Application No. PCT/US2012/069791 dated Feb. 5, 2015.

*Primary Examiner* — (Jackie) Tan-Uyen T Ho
*Assistant Examiner* — Joseph D Boecker
(74) *Attorney, Agent, or Firm* — Emory Patent Group

(57) ABSTRACT

Resuscitator devices including inflation control devices and the inflation control valves can prevent an excessive number of breaths per minute during manual resuscitation from being delivered to a patient. The inflation control valves are inlet valves for a resuscitator device having a flexible chamber that extends from a first end to a second end, the second end being configured to attach to an airway adjunct. The valve housing may be configured to be disposed about the first end and to receive air for inflating the flexible chamber, the valve housing being partially disposed within the flexible chamber. The inflation control member may be (Continued)

configured to control inflation rate of the flexible chamber, the inflation control member being disposed within the valve housing and movable with respect to the valve housing.

20 Claims, 5 Drawing Sheets

(56) References Cited

U.S. PATENT DOCUMENTS

| | | | | |
|---|---|---|---|---|
| 5,109,840 A * | 5/1992 | Daleiden | ............ | A61M 16/208 128/204.28 |
| 5,557,049 A * | 9/1996 | Ratner | ................ | A61M 16/208 128/204.23 |
| 5,628,305 A * | 5/1997 | Melker | ............ | A61M 16/0048 128/202.29 |
| 5,803,074 A * | 9/1998 | Pope | ................ | A61M 16/0084 128/203.11 |
| 6,070,574 A * | 6/2000 | O'Day | ............. | A61M 16/0048 128/202.28 |
| 6,253,767 B1 * | 7/2001 | Mantz | ............... | A61M 16/0078 128/205.13 |
| 6,578,574 B1 * | 6/2003 | Køhnke | ............ | A61M 16/0078 128/203.11 |
| 6,786,216 B2 | 9/2004 | O'Rourke | | |
| 6,792,947 B1 | 9/2004 | Bowden | | |
| 7,051,596 B1 * | 5/2006 | Lau | ................... | A61M 16/0078 73/716 |
| 7,861,710 B2 * | 1/2011 | Ingenito | ............... | A61M 11/008 128/200.24 |
| 2004/0211416 A1 * | 10/2004 | Lurie | .................... | A61M 16/20 128/203.11 |
| 2006/0060199 A1 | 3/2006 | Lampotang et al. | | |
| 2007/0267019 A1 * | 11/2007 | Lugtigheid | ......... | A61M 16/208 128/205.13 |
| 2008/0015475 A1 * | 1/2008 | Lau | ................... | A61M 16/0057 601/41 |
| 2008/0314386 A1 * | 12/2008 | Myklebust | ........ | A61M 16/0078 128/205.15 |
| 2009/0020128 A1 * | 1/2009 | Metzger | ............ | A61M 16/0825 128/207.16 |
| 2010/0236557 A1 * | 9/2010 | Reisman | ............ | A61M 16/0078 128/205.13 |

* cited by examiner

INFLATION CONTROL VALVES FOR RESUSCITATOR DEVICES AND RESUSCITATOR DEVICES

CROSS REFERENCE TO RELATED APPLICATION

This application claims priority to U.S. Provisional Application Ser. No. 61/576,160 filed on Dec. 15, 2011, which is hereby incorporated by this reference in its entirety.

BACKGROUND

A bag-valve-mask (BVM) is an essential airway management device found in most emergency and operating rooms, as well as emergency medical service organizations, worldwide. The BVM is a hand-held device often used, either with a facemask or in conjunction with another airway management device, such as an endotracheal tube (ET) or laryngeal mask airway (LMA), to provide oxygen and manually resuscitate a patient, for example, until a mechanical ventilator is attached.

Through proper ventilation technique, an operator can use a BVM to administer the right amount of oxygenated air to the patient through constant and steady manual pumping of the bag. However, proper ventilation technique generally requires comprehensive training. Nonetheless, even experienced operators can provide improper and inconsistent ventilation of the patient, and more specifically, hyperventilate a patient by over excessive manual pumping of the bag. Hyperventilation or over excessive bagging can result in reduced blood flow to vital organs and even brain ischemia.

U.S. Pat. No. 6,792,947 discloses a bag-valve-mask (BVM) device with a flow control valve interposed between the patient mask and bag to limit the gas flow from the bag to the mask. U.S. Pat. No. 5,109,840 discloses a directional control valve housing in a squeeze bag resuscitator that includes a duck-bill element that permits inhaling from the duck-bill opens, and spontaneous exhaling as the periphery of the duck-bill is pushed away from its seat. U.S. Pat. No. RE30,063 discloses a high pressure safety valve that automatically closes when high pressure conditions exist.

Thus, there is a need for a manual ventilation device that can provide proper and consistent rate of ventilation.

SUMMARY

The disclosure relates to inlet valves for resuscitator devices and resuscitator devices including an inlet valve configured to control the inflation of the resuscitator device. The disclosed resuscitator devices and inlet valves can prevent an excessive number of breaths per minute during manual resuscitation from being delivered to a patient by delaying inflation of the resuscitator device.

In some embodiments, the inlet valve may be configured for a resuscitator device having a flexible chamber that extends from a first end to a second end, the second end being configured to attach to an airway adjunct. The inlet valve may include a valve housing configured to be disposed at the first end and to receive air for inflating the flexible chamber, the valve housing being partially disposed within the flexible chamber; and an inflation control member configured to control a rate of inflation of the flexible chamber, the inflation control member being disposed within the valve housing and movable with respect to the valve housing.

In some embodiments, the disclosure relates to a resuscitator device. The resuscitator device may include a flexible chamber that extends from a first end to a second end, the second end being configured to deliver air to a patient through an airway adjunct; and an inlet valve disposed about the first end and partially disposed within the flexible chamber. The inlet valve may include: a valve housing configured to receive air for inflating the flexible chamber; and an inflation control member configured to control a rate of inflation of the flexible chamber, the inflation control member being disposed within the valve housing and movable with respect to the valve housing. In some embodiments, the resuscitator device may further include an airway adjunct disposed at the second end. The airway adjunct may include a face mask.

In some embodiments, the inflation control member may be configured to cause a predetermined delay between compression and inflation of the flexible chamber. The compression may be maximum compression and the inflation may be substantially full inflation. The inflation control member may be configured to allow the flexible chamber to inflate when the inflation control member is disposed at a first position with respect to the valve housing. The inflation control member may be configured to allow maximum compression of the flexible chamber when the inflation control member is disposed at a second position with respect to the valve housing. At the second position, the inflation control member may be configured to allow substantially full inflation of the flexible chamber.

In some embodiments, the valve housing may extend between a first end and a second end, the second end being closed. The inflation control member may include a spring and a platform. The spring may be fixedly disposed to the second end and the platform.

In some embodiments, the valve housing may include at least a first portion and a second portion, the second portion being configured to be disposed substantially within the flexible chamber. The second portion may include an outlet section configured to deliver air into the flexible chamber. The outlet portion may be configured to deliver air into the flexible chamber to cause the flexible chamber to inflate.

In some embodiments, the inflation control member may be configured to cause the flexible chamber to inflate when the control member is disposed between the outlet section and the closed end of the valve housing. In some embodiments, the inflation control member may be configured to permit one substantially full inflation per every about 5 seconds.

In some embodiments, the inflation control member may be configured to permit one maximum compression of the flexible chamber per every about 5 seconds. In some embodiments, the flexible chamber may be configured to deliver 700 mL of air during a maximum compression with one hand or 1100 mL or during a maximum compression with two hands.

In some embodiments, the compression or maximum compression may be manual.

In some embodiments, the disclosure may relate to a kit. In some embodiments, the kit may include a flexible chamber and an inlet valve. In some embodiments, the kit may further include an airway adjunct. In further embodiments, the kit may include a resuscitator device including the inlet valve.

DESCRIPTION OF THE DRAWINGS

The disclosure can be better understood with the reference to the following drawings and description. The components

DESCRIPTION OF THE EMBODIMENTS

Figure 1:
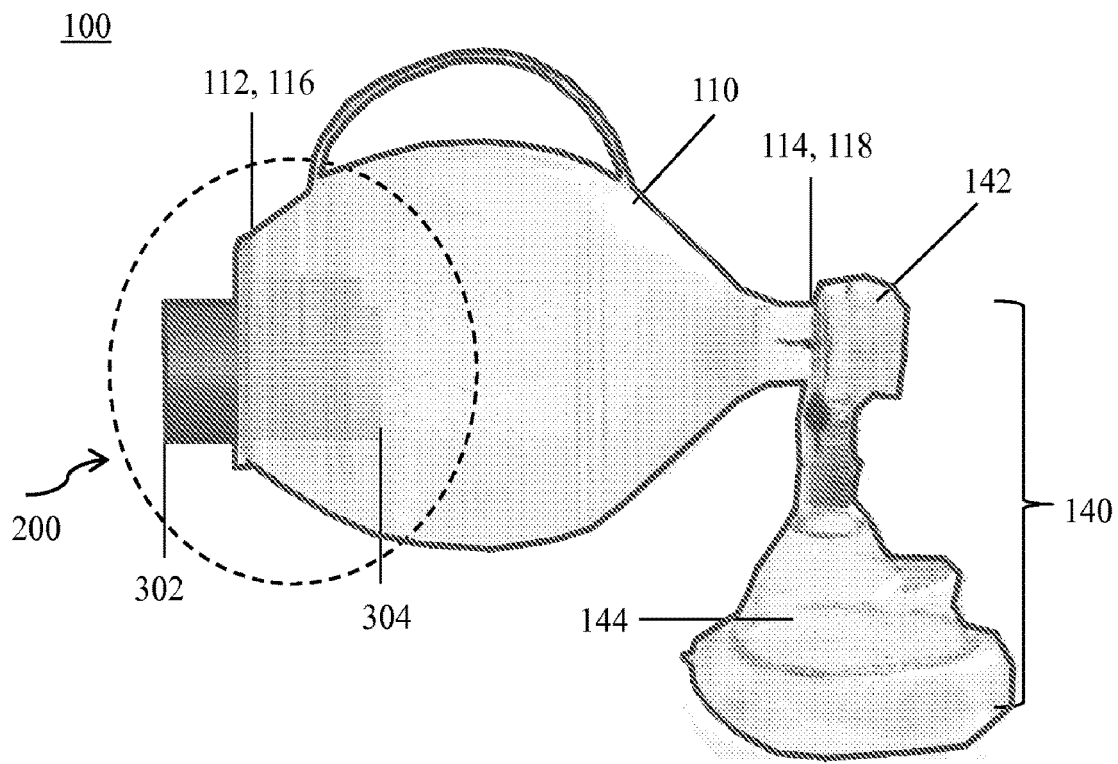
FIG. 1 illustrates a resuscitator device according to embodiments.
Figure 2:
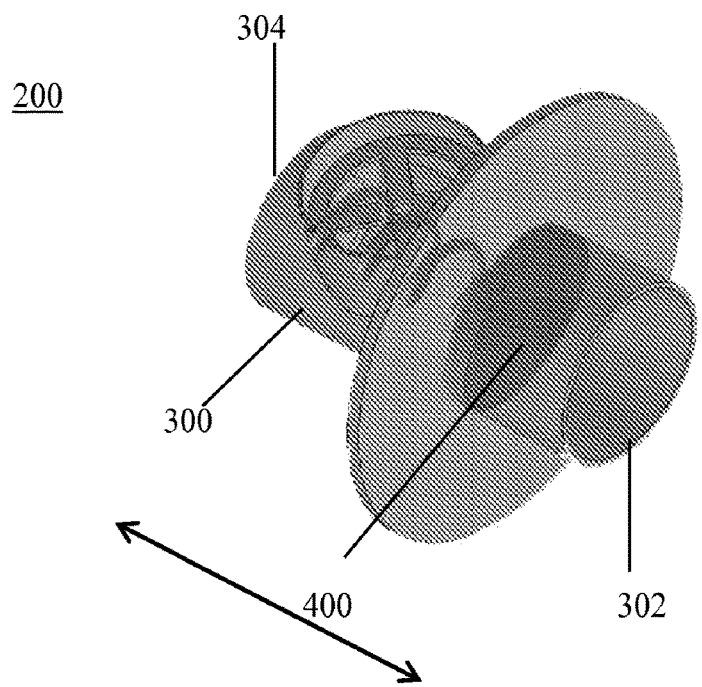
FIG. 2 illustrates an inlet valve device according to embodiments.
Figure 3:
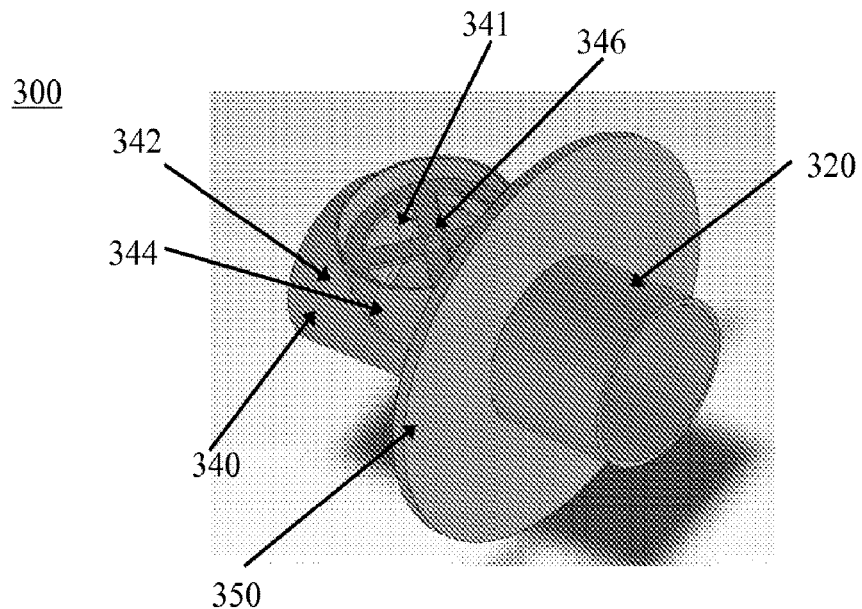
FIG. 3 illustrates a valve housing according to embodiments.
Figure 4:
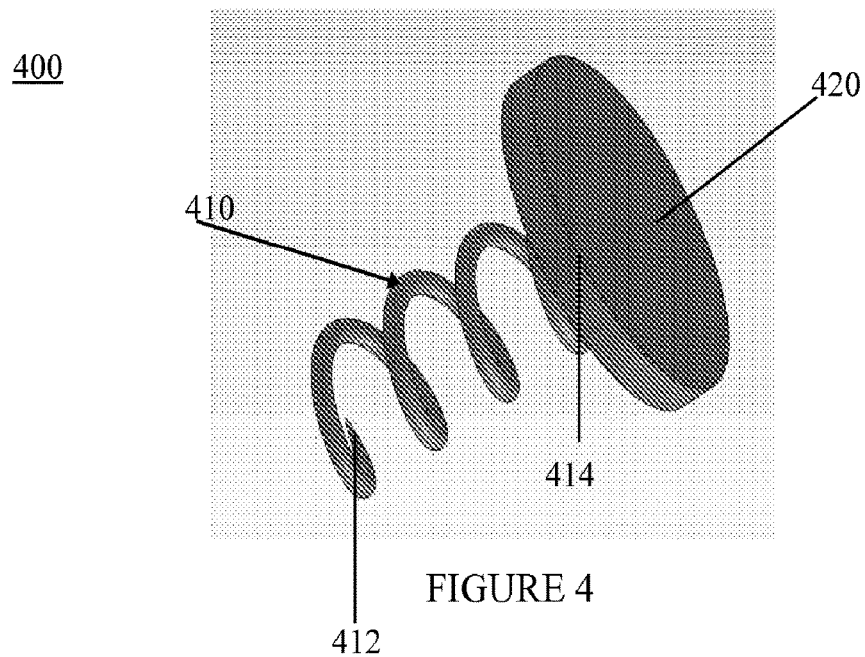
FIG. 4 illustrates an inflation control member according to embodiments.

The following description, numerous specific details are set forth such as examples of specific components, devices, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

The disclosed resuscitator devices and inflation control valves are configured to improve the manual ventilation of a patient. The disclosed valves are configured to regulate the time required to inflate the bag (i.e., the time rate of inflation of the resuscitator device) after a compression and thereby control the rate of ventilation of the patient. The disclosed valves are configured to cause a delay (when enabled) between compressions by delaying the inflation of the bag for a predetermined period of time following or after a compression. In some embodiments, the disclosed resuscitator devices and inflation control valves can be configured to ventilate the patient according to American Heart Association guidelines. The American Heart Association guidelines suggest that a breath of 700 ml of oxygenated air should be administered to an adult patient every 5 seconds during manual resuscitation. The disclosed resuscitator devices and inflation control valves can therefore prevent an excessive number of breaths per minute during manual resuscitation from being delivered to a patient.

FIG. 1 shows a resuscitator device (also referred to as a bag-valve mask (BVM) device) 100 according to embodiments. The resuscitator device 100 may include a flexible chamber (also referred to as "bag") 110. The flexible chamber 110 may be a hollow chamber configured to inflate and deflate. In some embodiments, the flexible chamber 110 may be made of a polymer material, for example, a styrene-ethylene-butylene-stryene based thermoplastic elastomer (SEBS) material.

The volume and/or dimensions of the flexible chamber 110 may vary. In some embodiments, the volume and/or dimensions of the flexible chamber 110 may depend on the volume to be delivered during compression with one hand and/or two hands. In some embodiments, the flexible chamber may be configured to deliver about 700 mL during compression with one hand or about 1000 mL of air to deliver compression with two hands. In some embodiments, the net bag reservoir volume, including the dead space of less than 6 mL, may be about $2FIGm1^3$. In other embodiments, the flexible chamber may be larger or smaller so as to be configured to deliver more or less volume, respectively.

The flexible chamber 110 may extend between an air inlet (also referred to as "first") end 112 and an air outlet (also referred to as "second") end 114. The air inlet end 112 and the air outlet end 114 may respectively include an air inlet opening 116 and air outlet opening 118. In some embodiments, the resuscitator device 100 may include an airway adjunct assembly 140 detachably attached to the outlet end 114. The airway adjunct assembly 140 may be any known assembly. In some embodiments, the airway adjunct assembly 140 may include a coupler 142 and an airway adjunct 144. The coupler 142 may include an outlet valve. The outlet valve, for example, may be a one-way valve configured to prevent carbon dioxide ($CO_2$) filled expired air (from the patient) from mixing with the air inside the flexible chamber. The outlet valve may also include an outlet for the expired $CO_2$ filled air. The airway adjunct 144 may include but is not limited to a face mask (as shown in FIG. 1), an endotracheal tube, a laryngeal mask airway, any known respiratory add-ons (e.g., heat and moisture exchanger (HME)) used during manual resuscitation, or a combination thereof.

In some embodiments, the device 100 may further include an inlet control valve device (also referred to "an inflation control valve," "inlet control valve," and "inlet valve") 200 disposed at the air inlet end 112. The inlet valve 200 may be configured to control the rate at which air (e.g., oxygenated air, ambient air, or a combination thereof and referred to as "air") is delivered to the patient by controlling the inflation rate of the flexible chamber 110.

In some embodiments, the inlet valve 200 may be configured to control the ventilation rate of patient, for example, by limiting the inflation rate of the flexible chamber 110 according to American Heart Association guidelines for an adult patient, for example, to about 1 inflation about every 5 seconds. The inlet valve 200 may be configured to delay inflation of the flexible chamber 110 for about 5 seconds after a compression so as to deliver about 700 ml of oxygenated air to a patient (according to the American Heart Association guidelines for an adult patient). In other embodiments, the inlet valve 200 may be configured to delay inflation of the flexible chamber 110 for a different predetermined (time) delay after compression. The inlet valve 200 may be configured so that a full, effective compression may be delivered after the delay. The inlet valve 200 can generally prevent the flexible chamber 110 from being compressed effectively during the delay because the flexible chamber 110 may not be substantially fully inflated until after the delay. An effective compression or maximum compression refers to a compression of the flexible chamber that can deliver a maximum volume of air, for example, when the flexible chamber is substantially fully inflated. By being configured to delay inflation between compressions, the inlet valve 200 can thereby be configured to control the maximum compression rate of the flexible chamber 110.

In some embodiments, the inlet valve 200 may be disposed partially within or inside the flexible chamber 110 so that a portion extends within the flexible chamber 110 and a portion protrudes from the air inlet end 112. In some embodiments, the inlet valve 200 may include a valve housing 300 and an inflation control member 400 disposed within the valve housing 300, as shown in FIGS. 1-4. In some embodiments, the valve housing 300 may be made of a rigid material, for example, a hard polycarbonate material. In some embodiments, the valve housing 300 may extend from a first end (also referred to as "open end" or "inlet end") 302 to a second end (also referred to as a "closed end" or "outlet end") 304. The length of the housing 300 may vary. In some embodiments, the length of the housing 300 may correspond to the desired inflation delay. The first end 302 may be configured to be open and the second end 304 may be configured to be closed. The valve housing 300 may be partially disposed within the flexible chamber 110. The valve housing 300 may partially extend within the flexible chamber 110 so that the second end 304 is disposed within the flexible chamber 110 and partially extend outside of or protrude partially from the first end 112 of the flexible chamber 110 so that the first end 302 is disposed outside of the flexible chamber 110.

In some embodiments, the valve housing 300 may include more than one portion. In some embodiments, the valve housing 300 may include a first portion 320 and a second portion 340. The valve housing 300 may include a third portion 350 disposed between the first portion 320 and the second portion 340.

In some embodiments, the first portion 320 may extend from the third portion 350 to the (open) first end 302. The first portion 320 may have a cylindrical shape. The first portion 320 may be substantially disposed outside the flexible chamber 110. The first portion 320 may protrude from the first end 112 of the flexible chamber 110. The first end 302 may be configured to receive air from the atmosphere and/or oxygen tank.

In some embodiments, a one-way intake valve disc may be disposed on the first end 302. In some embodiments, the intake valve disc may be similar to an AMBU inlet valve. The intake valve may be made of a silicone material. As shown a prototype of a resuscitator device 800 in FIG. 8, an intake valve disc 822 may be disposed at the open end of a valve housing 820.

In some embodiments, the resuscitator device 100 may be configured to be connected to other devices, for example, an oxygen tank. In some embodiments, the first end 302 may be configured to connect to an oxygen tank to supplement ambient air with oxygenated air.

In some embodiments, the second portion 340 may extend from the second end 304 to the third portion 350. The second portion 340 may include more than one section. The second portion 340 may include a cylindrical section 342 that extends parallel with the first portion 320 and that has a cylindrical shape. The second portion 340 may also include an outlet portion 344 that extends perpendicular to the first portion 320 and the cylindrical section 342. The outlet portion 344 may include an opening (also referred to as "valve opening") 341. In some embodiments, the opening 341 may include an air vent 346 on which a one-way valve disc may be disposed. In some embodiments, the one-way valve disc may be a silicone and/or AMBU inlet valve like valve disc 822. The air vent 346 may be configured to deliver the air into the flexible chamber 110 that can cause the flexible chamber 110 to inflate.

In some embodiments, the inner diameter of the first portion 320 may be substantially the same as the inner diameter of the cylindrical section 342 of the second portion 340. In other embodiments, the diameters may be different.

In some embodiments, the third portion 350 may be a ring-shaped member that extends radially from the first portion 320 and second portion 340. The third portion 350 may be disposed at the first end 112 and may surround the opening 116. In some embodiments, the third portion 350 may be disposed outside of the flexible chamber 110. In other embodiments, the third portion 350 may be disposed inside of the flexible chamber 110.

In some embodiments, the inflation control member 400 may be configured to control the rate of manual compression of the flexible chamber 110 by controlling the rate of inflation of the flexible chamber 110 and thereby control the ventilation of a patient. In some embodiments, the inflation control member 400 may include a spring 410 and a platform 420 (also referred to a "stopper"). In other embodiments, the inflation control member 400 may include any biasing and/or damping system, for example, an ultra-low resistance hydraulic damper.

In some embodiments, the spring 410 may be between the closed end 304 of the valve housing 300 and the platform 420. Ends 412 and 414 of the spring 410 may be permanently disposed at the closed end 304 of the valve housing 300 and a surface of the platform 420, respectively, by a fastener (e.g., adhesive). In other embodiments, the spring 410 may be removably disposed at the closed end 304 of the valve housing 300, for example, so that the inflation control member 400 may be removed from the valve housing 300.

In some embodiments, the spring 410 may have a tension that is fixed or the spring 410 may be configured to have an adjustable tension. In some embodiments, the spring 410 may have a tension corresponding to the desired delay between compressions and/or inflation rate. In other embodiments, the inflation control member 400 may further include an adjustable tensioning member configured to adjust the tension of the spring 410. The adjustable tension member may be, for example, a screw or a knob.

In some embodiments, the platform 420 may have a circular shape. The platform 420 may have a diameter that substantially corresponds to the inner diameter of the first section 320 and/or the cylindrical section 342 of the inner housing 300, for example, so that it may be configured to substantially prevent air from entering the inner housing 300.

Figure 5:
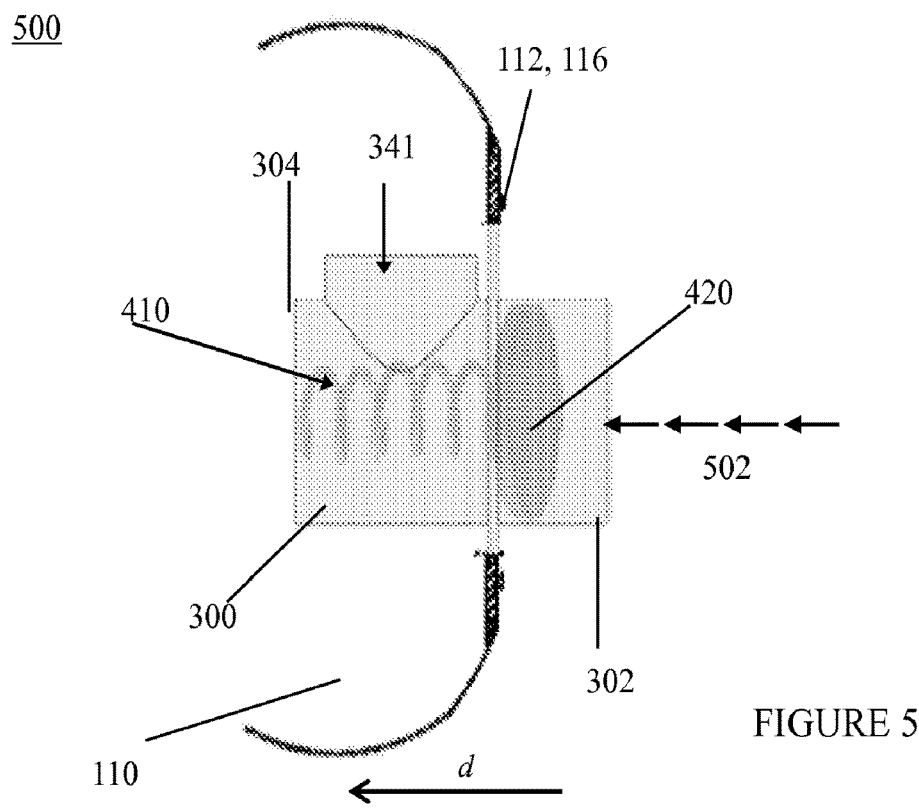
FIG. 5 illustrates a resuscitator device within an inflation control member in a position according to embodiments.
Figure 6:
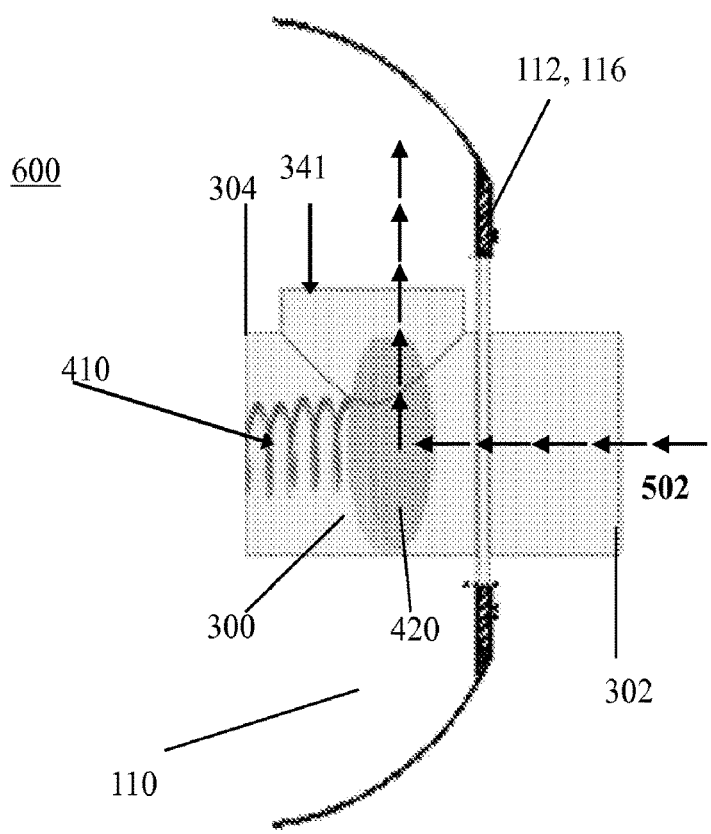
FIG. 6 illustrates a resuscitator device within an inflation control member in another position according to embodiments.

The inflation control member 400 may be configured to include a delay between at least two positions, (i) a first position (also referred to as an "inflation" position) in which the flexible chamber 110 may inflate (e.g., air may be allowed to enter the inlet valve) and the flexible chamber 110 can be prevented or unable from being compressed effectively (i.e., the flexible chamber being capable of delivering a maximum volume of air) as shown in example 600 in FIG. 6; and (ii) a second position (also referred to as "compressed" position") immediately following compression as shown in example 500 in FIG. 5. The inflation control member 400 may be configured to delay the movement between inflation and compression positions according to a predetermined time delay (period). As mentioned above, the predetermined time delay may correspond to about 5 seconds, in some embodiments.

The inflation control member 400 may be configured to control the inflation rate due to the pressure differential forces and thereby control the ventilation rate of the flexible chamber 110. After or following compression of the flexible chamber 110, the platform 420 may be disposed toward the open end (also referred to as "first end") 302 of the housing 300, as shown in FIG. 5. In this position (e.g., with the spring lengthened or extended), the inflation control member 400 can be configured to substantially prevent or block air 502 from entering the flexible chamber 110 and thereby substantially prevent the inflation of the flexible chamber 110. As shown in FIG. 5, the platform 420 can be configured to substantially prevent air 502 from entering and inflating the flexible chamber 110. The platform 420 may be configured to substantially prevent air 502 from entering and inflating the flexible chamber 110 by being disposed between the valve opening 341 and the open end 302 for a predetermined delay period d. The pressure differential force (after a compression) can cause the spring 410 to compress and move the platform 420 towards the valve opening 341. Once the platform 420 advances toward the closed end (also referred to as "second end") 304 and passes the valve opening 341, air 502 can rush back into the flexible chamber 110, causing the reinflation of the flexible chamber 110, for example, as shown in FIG. 6. The inflation control valve 400 may be configured to cause the platform 420 to pass the valve opening 341 after the predetermined delay period d. Once the flexible chamber 110 is substantially fully inflated, there is generally no more pressure differential and the spring 410 can recoil to its unextended state. The elastic force of the spring 410 can thereby cause the platform 420 to move towards the closed end 304. In this position, the flexible chamber 110 is substantially fully inflated and the operator can now deliver an effective or maximum compression to a patient when compressing the flexible chamber 110.

In some embodiments, the inlet valve 200 may be disabled. In some embodiments, the inlet valve 200 may include a locking member configured to lock the inflation control member 400 in a disabled position. In other embodiments, a part or the entire inlet valve 200 may be configured to be removed from the flexible chamber 110. For example, the inflation control member 400 may be configured to be removably disposed within the inflation control valve 200 so that it may be removed when an unaltered one way valve-system is desired.

In some embodiments, the inlet valve 200 may further include a supporting frame 700 configured to minimize friction of the inflation control member 400. The supporting frame 700 may be disposed within the valve housing 300. In other embodiments, the supporting frame 700 may be omitted.

Figure 7:
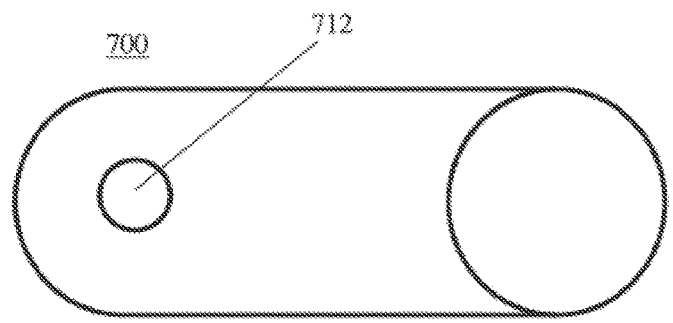
FIG. 7 illustrates a support member according to embodiments.
Figure 10:
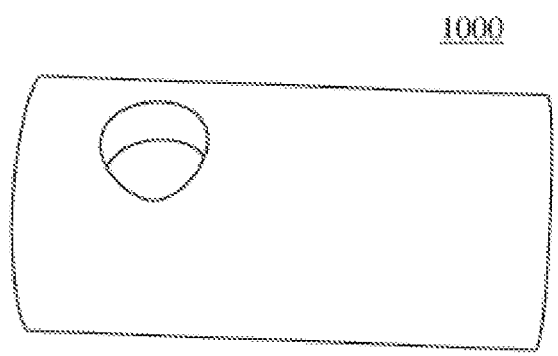
FIG. 10 illustrates an example of a support member according to embodiments.

In some embodiments, the support member 700 may have a cylindrical shape, as shown in FIGS. 7 and 10. In some embodiments, the support member 700 may be disposed between the valve housing 300 and the inflation control member 400. The support member 700 may have an opening 712 configured to be aligned with the opening 341 of the valve housing 300. The support member 700 may have a length that corresponds to the length of the valve housing 300. The support member 700 may be made of a rigid material. In other embodiments, the support member 700 may be any structure configured to reduce friction. For example, the support member 700 may be a stem disposed within the spring 410.

Figure 8:
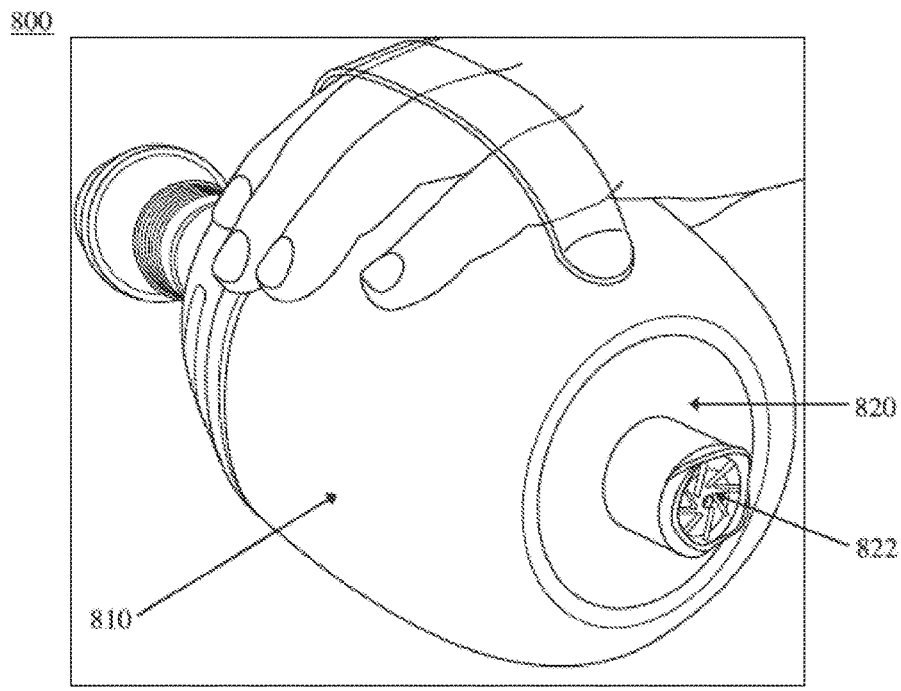
FIG. 8 illustrates an example of a prototype of a resuscitator device according to embodiments.
Figure 9:
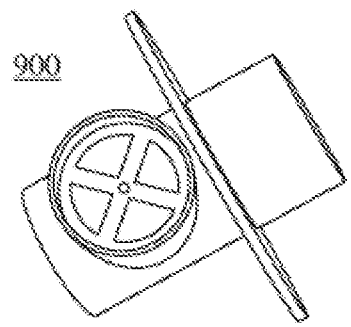
FIG. 9 illustrates an example of a prototype of a valve housing according to embodiments.

FIGS. 8-10 illustrate examples of prototypes of the resuscitator device and inlet valve according to embodiments. FIG. 8 shows a resuscitator device 800 including a flexible chamber 810 and an inlet valve 820 according to embodiments. FIG. 9 shows a valve housing 900 and FIG. 10 shows a support frame 1000 according to embodiments.

According to some embodiments, the disclosed resuscitator devices and inlet valves may be single use or be disposable. In some embodiments, the resuscitator devices and compression inlet valves may be disposable. According to some embodiments, a portion or any combination of the disclosed resuscitator devices and inlet valves may be sold as a kit.

In some embodiments, the kit may include at least flexible chamber with an inlet valve. In further embodiments, the kit may further include an airway adjunct.

While various embodiments of the disclosure have been described, the description is intended to be exemplary rather than limiting and it will be apparent to those of ordinary skill in the art that may more embodiments and implementations are possible that are within the scope of the disclosure.

What is claimed:

1. An inlet valve for a resuscitator device having a flexible chamber that extends from a first end to a second end, the second end being configured to attach to an airway adjunct, comprising:
   a valve housing configured to be disposed at the first end of the flexible chamber and to receive air for inflating the flexible chamber, the valve housing being partially disposed within the flexible chamber,
   the valve housing extending between a first end and a second end that is parallel to and opposes the first end,
   the first end of the valve housing including an opening,
   the second end of the valve housing being closed and being configured to be disposed within the flexible chamber,
   the valve housing including a first portion, a second portion, and a third portion that are disposed between the first end and the second end of the valve housing,
   the third portion being disposed between the first portion and the second portion,
   the first portion including the first end of the valve housing and including a one-way valve disposed at the opening of the first end of the valve housing, the one-way valve being configured to intake the air for inflating the flexible chamber,
   the second portion including the second end of the valve housing and an outlet section that includes an opening,
   the outlet section being configured to deliver the air into the flexible chamber and extending perpendicular to the first end and the second end of the valve housing; and
   an inflation control member configured to control a rate of inflation of the flexible chamber, the inflation control member being disposed within the valve housing and movable with respect to the valve housing between the first end and the second end of the valve housing.

2. The valve according to claim 1, wherein the inflation control member is configured to cause a predetermined delay between substantially full inflation and compression of the flexible chamber.

3. The valve according to claim 1, wherein:
   the inflation control member is configured to move within the valve housing between at least a first position and a second position; and
   the inflation control member is configured to allow the flexible chamber to inflate when the inflation control member is disposed at the first position with respect to the valve housing.

4. The valve according to claim 3, wherein the inflation control member is configured to allow maximum compression of the flexible chamber when the inflation control member is disposed at the second position with respect to the valve housing.

5. The valve according to claim 1, wherein:
the inflation control member includes a spring and a platform;
the spring is fixedly disposed to the second end of the valve housing and the platform; and
the platform is parallel to the first end and the second end of the valve housing.

6. The valve according to claim 1, wherein:
the first portion is configured to be disposed substantially outside of the flexible chamber; and
the second portion is configured to be disposed substantially within the flexible chamber.

7. The valve according to claim 1, wherein the inflation control member is configured to allow the flexible chamber to inflate when the control member is disposed between the outlet section and the second end of the valve housing.

8. The valve according to claim 1, wherein the inflation control member is configured to permit one maximum compression per every about 5 seconds.

9. The valve according to claim 1, wherein:
the valve housing is rigid;
the second portion includes a cylindrical section that extends parallel to the first portion and has a cylindrical shape, the cylindrical section including the outlet portion being disposed perpendicular to the third portion; and
the third portion extends radially from the first portion and the second portion.

10. A resuscitator device, comprising:
a flexible chamber that extends from a first end to a second end, the second end of the flexible chamber being configured to deliver air to a patient through an airway adjunct; and
an inlet valve disposed at the first end of the flexible chamber and partially disposed within the flexible chamber, the inlet valve including:
a valve housing configured to receive air for inflating the flexible chamber,
the valve housing extending between a first end and a second end that is parallel to and opposes the first end of the valve housing,
the first end of the valve housing including an opening and disposed outside of the flexible chamber,
the second end of the valve housing being closed and disposed within the flexible chamber;
a one-way valve disposed at the opening of the first end of the valve housing and configured to intake the air for inflating the flexible chamber; and
an inflation control member configured to control a rate of inflation of the flexible chamber, the inflation control member being disposed within the valve housing and movable with respect to the valve housing between the first end and the second end of the valve housing.

11. The resuscitator device according to claim 10, further comprising:
an airway adjunct assembly disposed at the second end of the flexible chamber.

12. The resuscitator device according to claim 11, wherein:

the inflation control member is configured to move within the valve housing between at least a first position and a second position; and
the inflation control member is configured to allow the flexible chamber to inflate when the inflation control member is disposed at the first position with respect to the valve housing.

13. The resuscitator device according to claim 12, wherein the inflation control member is configured to allow maximum compression of the flexible chamber when the inflation control member is disposed at the second position with respect to the valve housing.

14. The resuscitator device according to claim 10, wherein:
the inflation control member includes a spring and a platform; and
the spring is fixedly disposed to the second end of the valve housing and the platform.

15. The resuscitator device according to claim 10, wherein:
the valve housing includes a first portion and a second portion, the first portion being disposed substantially outside of the flexible chamber and including the first end of the valve housing, the second portion being disposed substantially within the flexible chamber and including the second end of the valve housing; and
the second portion including an outlet section that includes an opening and is configured to deliver air to into the flexible chamber, the outlet section extending perpendicular to the first end and the second end of the valve housing.

16. The resuscitator device according to claim 15, wherein the inflation control member is configured to allow the flexible chamber to inflate when the control member is disposed between the outlet section and the second end of the valve housing.

17. The resuscitator device according to claim 10, wherein the inflation control member is configured to permit one maximum compression of the flexible chamber per every about 5 seconds.

18. The resuscitator device according to claim 10, wherein the flexible chamber is configured to deliver 700 mL of air during a maximum compression with one hand or 1100 mL of air during a maximum compression with two hands.

19. The resuscitator device according to claim 10, wherein the inflation control member is configured to cause a predetermined delay between compression and substantially full inflation of the flexible chamber.

20. The resuscitator device according to claim 15, wherein:
the second portion includes a cylindrical section that extends parallel to the first portion and has a cylindrical shape, the cylindrical section including the outlet portion;
the valve housing includes a third portion that is disposed between the first portion and the second portion and that extends radially from the first portion and the second portion; and
wherein the third portion is disposed at the first end of the flexible chamber.

* * * * *